United States Patent
Angeletakis et al.

(10) Patent No.: US 6,455,029 B1
(45) Date of Patent: Sep. 24, 2002

(54) DENTAL IMPRESSION MATERIAL UTILIZING RUTHENIUM CATALYST

(75) Inventors: Christos Angeletakis, Orange; Mingfei Chen, Monterey Park, both of CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 09/690,236

(22) Filed: Oct. 17, 2000

(51) Int. Cl.⁷ .............. A61K 7/16; C08L 83/05; C08L 5/24; C08L 3/34
(52) U.S. Cl. ............. 424/49; 523/107; 523/109; 524/264; 524/448
(58) Field of Search ............. 424/49; 523/107, 523/109; 524/448, 264

(56) References Cited

U.S. PATENT DOCUMENTS

| | | |
|---|---|---|
| 5,266,670 A | 11/1993 | Nakos et al. |
| 5,728,785 A | 3/1998 | Grubbs et al. |
| 6,075,068 A | 6/2000 | Bissinger |
| 6,121,362 A * | 9/2000 | Wanek et al. ............ 524/448 |

FOREIGN PATENT DOCUMENTS

| | | |
|---|---|---|
| EP | 1 025 830 | 8/2000 |

OTHER PUBLICATIONS

"Surface–inititated ring–opening metatheis polymerization on si/sio2", Kim et al., 2000, Macromolecules, 33(8), 2793–2795.*

International Organization for Standardization, Dental Elastomeric Impression Materials, ISO 4823 (1992).

Scholl et al., Synthesis and Activity of a New Generation of Ruthenium–Based Olefin Metathesis Catalysts Coordinated with 1,3–Dimesityl–4,5–dihydroimidazol–2–ylidene Ligands, Org. Lett., vol. 1, No. 6, 953–956 (1999).

Chevalier et al., Ring–Opening Olefin Metathesis Polymerisation (ROMP) as a Potential Cross–Linking Mechanism for Siloxane Polymers, J. of Inorganic and Organometallic Polymers, vol. 9, No. 3, 151–164 (1999).

* cited by examiner

*Primary Examiner*—Marianne C. Seidel
*Assistant Examiner*—Brian-Yong Kwon
(74) *Attorney, Agent, or Firm*—Wood, Herron & Evans, LLP

(57) ABSTRACT

A composition for use as a dental impression material including a polymerizable telechelic oligomer or polymer curable by ring-opening metathesis polymerization, a filler system, and a ruthenium carbene complex catalyst, whereby the catalyst initiates ring-opening metathesis polymerization of the composition. The invention includes a paste/paste system in which a base paste includes the polymerizable telechelic oligomer or polymer and a filler system and in which a catalyst paste includes the catalyst dissolved in an inert solvent and a filler system. The telechelic oligomer or polymer may be, for example, a polydimethylsiloxane end-functionalized with norbornenyl groups. The catalyst may be, for example, a ruthenium carbene complex with a ligand having a basicity higher than tricyclohexylphosphine. The composition of the present invention exhibits reduced sensitivity to sulfur impurities.

34 Claims, No Drawings

DENTAL IMPRESSION MATERIAL UTILIZING RUTHENIUM CATALYST

FIELD OF THE INVENTION

This invention relates to dental impression materials.

BACKGROUND OF THE INVENTION

Impression materials used in dentistry are one of several types of elastomers, such as polysulfides, condensation silicones, polyethers or polyvinyl siloxanes (addition-curable silicones). These materials are normally two-paste systems that are mixed immediately before use, then placed in contact with the tooth structure. Mixing of the two pastes initiates a chemical reaction that results in the formation of the elastic rubber impression material after setting, thereby forming a negative impression of the tooth structure involved. The addition-curable silicones, which exhibit fast curing speeds and low shrinkages, typically use a platinum-containing hydrosilation catalyst. This type of catalyst necessitates the use of silicon-containing oligomers, which are generally expensive. Also, the platinum-based catalyst can be inactivated by sulfur-containing impurities present in the latex gloves ordinarily used by dentists, as well as by certain medicaments used in the oral cavity. In addition, there may be undesirable hydrogen evolution from the decomposition of the hydrosiloxane cross-linkers that are present in the systems. This may increase the time and effort necessary to take an impression with these materials because extra precautionary steps have to be taken.

In view of these drawbacks, there is a need for dental impression materials that do not exhibit the various sensitivity problems described above.

SUMMARY OF THE INVENTION

The present invention provides a composition for use as a dental impression material. The composition comprises a polymerizable telechelic oligomer or polymer curable by ring-opening metathesis polymerization (ROMP), a filler system, and a ruthenium carbene complex catalyst, whereby the catalyst initiates the ring-opening metathesis polymerization of the composition. In an embodiment of the invention, the composition is a paste/paste system in which a base paste includes the polymerizable telechelic oligomer or polymer and a filler system and in which a catalyst paste includes the catalyst dissolved in an inert solvent and a filler system. In one example of the invention, the telechelic oligomer or polymer is a polydimethylsiloxane end-functionalized with norbornenyl groups and having between 5 and 5000 dimethylsiloxane units, and the catalyst is a ruthenium carbene complex with at least one of the ligands having a basicity higher than tricyclohexylphosphine. The composition of the present invention exhibits reduced sensitivity to sulfur impurities.

DETAILED DESCRIPTION OF THE INVENTION

The present invention provides formulations for dental impression materials using a telechelic resin system that is cured by ROMP with the aid of a catalyst based on a ruthenium complex. The composition of the present invention comprises a catalyst paste and base paste in intimate admixture with one another in a paste/paste system. Curing is obtained by a ROMP reaction using a ruthenium carbene as a catalyst. Generally, in this system, the catalyst paste comprises a ruthenium catalyst for initiating polymerization, a solvent for the catalyst that is miscible or dispersible with the base paste, and fillers for optimizing viscosity for the application of the paste and for reinforcement of the cured material. Fillers for non-reinforcing purposes can always also be used. The base paste generally comprises a polymerizable oligomer and/or polymer resin system that is curable via the ROMP mechanism, and fillers as described above for the catalyst paste.

The type of oligomers and/or polymers that may be used in the present invention include telechelic (end functionalized) polymers with any of a variety of backbones, as long as the chain ends are functionalized with groups reactive by ROMP, such as norbornenyl groups. For example, the resin may be a telechelic polydimethylsiloxane terminated with 2-(5-norbornenyl)ethyl groups according to the following structure:

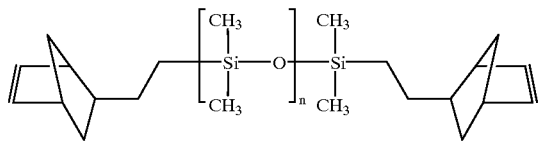

where n=5–5000, for example 27–1590. Other examples of telechelic polysiloxanes are those having the following structure:

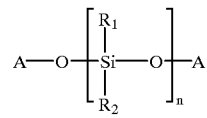

where n = 5–5000, such as 27–1590;

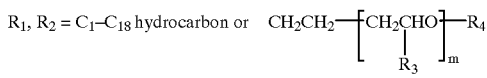

where $R_3$, $R_4$ = $C_1$–$C_{18}$ hydrocarbon, and m = 0–2; and

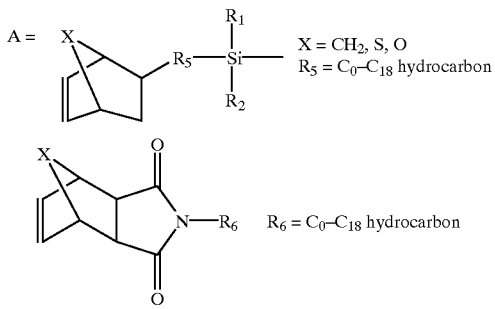

For an alternative example, the resin may be polytetrahydrofuran-polyethylene oxide copolymer terminated with norbornenyl groups. As yet another alternative example, the resin may be a norbornenyl carboxylate terminated polybutadiene.

The catalysts useful in the present invention include the ruthenium carbene complexes. The parent benzylidene ruthenium complex A, with the following structure, exhibits high air and water stability:

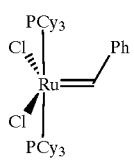

A

The ring-opening metathesis activity of the parent complex A can be increased by substituting a saturated imidazole ligand for a tricyclohexylphosphine ligand. The ligands may be 4,5-dihydroimidazol-2-ylidenes, which have the following general structure:

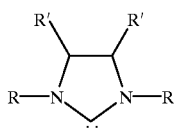

These substituted ligands have a basicity higher than that of tricyclohexylphosphine, as indicated by a higher pKa, which is believed to contribute to the higher activity. Ruthenium complex B, a derivative of complex A and having the structure shown below, is a substituted ruthenium carbene complex including such a ligand:

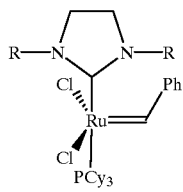

B

Other derivatives of parent complex A can also be used in the resin system of the composition of the present invention, such as substituted ruthenium carbene complexes C and D having the following structures:

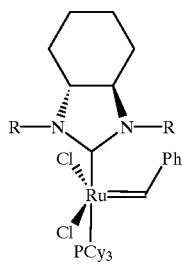

C

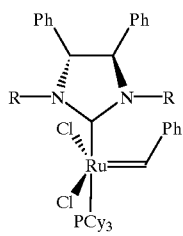

D

The catalyst component of the dental impression material is formulated by dissolving the ruthenium carbene complex in an inert solvent. The solvent, or diluent, is chosen such that the solvent and the complex are miscible (soluble) or dispersible with the base pastes, and such that the solvent does not interfere with the reaction. The solvent may be, for example, 3-phenyl-heptamethyl-trisiloxane.

The fillers useful in the composition of the present invention include reinforcing and/or non-reinforcing (extending) fillers. Suitable reinforcing fillers include precipitated silicas, fumed silica, calcium silicate (Wollastonite), crystalline silica, and the like. The addition of reinforcing filler improves the mechanical strength, such as tensile and tear strengths, of the cured composition. Suitable non-reinforcing fillers include diatomaceous earth, aluminas, magnesias, titanium dioxide, zirconium silicate, calcium carbonate, metallic oxides, and the like. Surface-treated fillers may also be used. Typical surface treatments include silanization and the like. In accordance with the present invention, mixtures of fillers with different particle sizes may be used. A bimodal filler system blended with sub-micron (<1 μm) and micronsized particles (2–10 μm) of close particle size distribution is used as a varying filler loading to provide dental impression materials with low, medium or high consistency, as defined by ISO Specification No. 4823 (2nd. Ed. 1992), suitable for use in all dental impression techniques. The filler may be present in amounts of from about 15 wt. % to about 50 wt. % of the composition. To adjust the consistency of the two-paste embodiment of the present invention to achieve either a low, medium or high consistency composition, the sub-micron sized filler and/or the micron sized filler may be adjusted in one or both of the catalyst and base pastes. The higher the consistency desired, the more beneficial it is to increase the sub-micron filler to a greater extent than the increase in the micron sized filler, whereby the sub-micron filler particles are worked into the interstitial spaces between micronized particles during mixing.

By way of example only and not limitation, the composition may comprise the polymerizable resin in an amount of about 5 wt. % to about 95 wt. %, the sub-micron sized filler in an amount up to about 10 wt. %, the micron sized filler in an amount of about 10 wt. % to about 60 wt. %, and the catalyst in an amount of about 0.001 wt. % to about 1 wt. %. The composition of the present invention may further include optional additives known to one skilled in the art, such as pigments, that do not interfere with the reaction.

EXAMPLE

A telechelic polydimethylsiloxane terminated with norbornyl groups was synthesized according to the following scheme:

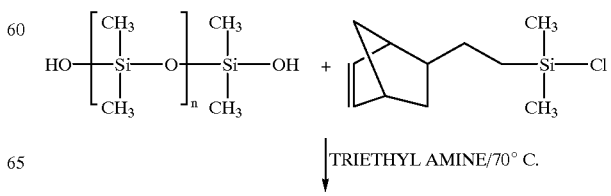

TRIETHYL AMINE/70° C.

-continued

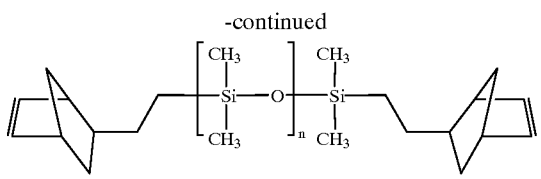

A three-neck round bottom flask equipped with a mechanical stirrer, a condenser and $N_2$ inlet-outlet was charged with 360.0 g silanol terminated poly(dimethyl siloxane) (DMS-S27, n=243, from Gelest Corp.) and 4.85 g triethylamine containing 1% 4-(N,N-dimethyl)amino-pyridine. A quantity of 9.02 g of 2-(5-norbornenyl)-ethyl-dimethylchlorosilane was added dropwise to the flask with stirring. After the addition, the reaction temperature was raised to 70° C., and stirring was continued for 4 hours at that temperature. Then, 2 mL methanol was added to the mixture and stirring was continued for 1 hour longer. The reaction mixture was next diluted with 500 mL of hexanes and filtered to remove the white salt. The hexane solution was washed three times with 1% HCl and three times with deionized water. The solution was then dried over $Na_2SO_4$. After evaporation of the solvent under vacuum, a clear liquid product was obtained. This compound 1, having n=243 (average), exhibited the following infrared peaks (cm$^{-1}$): 2963, 1411, 1260, 1020, 800, and 702.

A second compound was produced following the same procedure as above, but this time using a silanol terminated poly(dimethyl siloxane) having n=27 average). These two resulting compounds were then mixed and compounded with fillers and dispersed in a three-roll mill to form a suspension. This suspension is referred to as the base component, or base paste, and its composition is detailed in Table 1.

TABLE 1

Test Base Paste Composition

| | |
|---|---|
| Compound 1, n = 243 | 55.25 wt. % |
| Compound 1, n = 27 | 9.75 wt. % |
| Calcium Silicate Wollastonite (2–10 μm average particle size) | 30 wt. % |
| Sub-micron Silica (<1 μm average particle size) | 5 wt. % |
| Total | 100 |

Two catalyst pastes were then formulated by dissolving in 3-phenyl-heptamethyl-trisiloxane the ruthenium carbene complex A and B, respectively, each catalyst complex having been obtained from Strem Chemicals Inc., Newburyport, Mass. The solutions were then compounded with fillers and dispersed in a three-roll mill to form suspensions. These suspensions are referred to as the catalyst components, or catalyst pastes, and are further described in Table 2.

TABLE 2

Test Catalyst Paste Compositions

| | |
|---|---|
| 3-phenyl-heptamethyl-trisiloxane | 64.35 wt. % |
| Calcium Silicate Wollstonite (2–10 μm average particle size) | 30 wt. % |
| Sub-micron Silica (<1 μm average particle size) | 5 wt. % |
| Catalyst A or Catlyst B | 0.65 wt. % |
| Total | 100 |

For comparative purposes, the test base paste composition was combined with each of the test catalyst paste compositions in a base to catalyst ratio of 10:1 and mixed by spatulation. Separately, for use in the comparison, catalyst and base pastes were prepared for an addition-curable silicone composition using a platinum-containing hydrosilation catalyst. The comparative control base paste and control catalyst paste compositions are detailed in Tables 3 and 4, respectively.

TABLE 3

Control Base Paste Composition

| | |
|---|---|
| Polyvinyldimethylsiloxane (4000 cSt.) | 57 wt. % |
| Calcium Silicate Wollastonite (2–10 μm average particle size) | 30 wt. % |
| Sub-micron Silica (<1 μm average particle size) | 5 wt. % |
| Polymethylhydrosiloxane crosslinker (30 cSt.) | 8 wt. % |
| Total | 100 |

TABLE 4

Control Catalyst Paste Composition

| | |
|---|---|
| Polyvinyldimethylsiloxane (4000 cSt.) | 63.5 wt. % |
| Calcium Silicate Wollastonite (2–10 μm average particle size) | 30 wt. % |
| Sub-micron Silica (<1 μm average particle size) | 5 wt. % |
| Platinum Catalyst Complex with Vinylsiloxane | 1.5 wt. % |
| Total | 100 |

The control pastes were combined in a base paste to catalyst paste ratio of 1:1.

Both the test compositions and control compositions are classified as type 2 or 3 impression materials, meaning that they have low to medium consistency, as defined by ISO Specification No. 4823. The physical properties of the cured compositions were determined using ISO Specification No. 4823 for evaluation of work time, set time, mixed consistency, dimensional change, strain and compression and deformation recovery. The results are given below in Table 5.

Table 5 also includes the results of a test devised to determine the relative sensitivity of these formulations to residual sulfur compound containing surfaces, such as latex gloves used by dentists. The sulfur sensitivity test comprised preparing a 1% solution of an approximately 30%/70% mixture of mono- and di-octyl tin bis (2-ethylhexylthiolycolate) esters in hexane. A microbrush was dipped in this solution, and the solution was painted on the edge of a 3×6 inch dental impression mixing pad. The control base paste and the control catalyst paste were mixed in a 1:1 ratio (0.5 g/0.5 g) and the test base paste and the test catalyst paste were mixed in a 10:1 ratio (1.0 g/0.1 g), each by spatulation for 20 seconds, and each mixture was partially placed on top of the area of the pad where the hexane solution was painted on. After the bulk of the material had set, as indicated by set time and recovery from deformation, the mixture was lifted off the pad, and the area that was in contact with the painted area was checked to see if it had also set. The materials were checked 10 minutes after placement on the pad to ascertain whether setting was achieved at the sulfur contact area after the bulk material had already set. The results of this sulfur sensitivity test, along with the physical properties set forth in ISO Specification No. 4823 are set forth in Table 5.

TABLE 5

Physical Properties of Impression Material Pastes

| | ISO 4823 Specification (Type 2 and 3) | Control | Test 1 | Test 2 |
|---|---|---|---|---|
| Catalyst Used | | Pt Complex | Complex A | Complex B |
| Mixing Ratio (Base:Catalyst) | | 1:1 | 10:1 | 10:1 |
| Consistency (mm) | ≧36: Type 3 31–9: Type 2 | 34.7 (0.6) | 43 (1) | 33 (2) |
| Work Time (sec.) | >30 | 235 (13) | 198 (10) | 181 (8) |
| Set Time (sec.) | | 587 (8) | 400 (10) | 327 (12) |
| Strain in Compression (%) | 2–20 | 5.5 (0.2) | 10.7 (0.6) | 6.4 (0.0) |
| Deformation Recovery (%) | 96.5–100 | 99.4 (0.1) | 99.4 (0.1) | 99.8 (0.0) |
| Linear Dimensional Change (after 24 h) (%) | 0–1.5 | 0.06 (0.08) | 0.08 (0.01) | 0.11 (0.02) |
| Detail Reproduction | required | yes | yes | yes |
| Compatibility with Gypsum | required | yes | yes | yes |
| Sulfur Sensitivity | | No full or partial set in 20 min. | No full set; Partial set after 10 min. | Full set after 10 min. |

From the data in Table 5, it is shown that the materials of the present invention pass the requirements of ISO specification 4823 for Type 2 and/or 3 dental impression materials, including requirements for compatibility with gypsum and detail reproduction.

In addition, the test impression materials exhibited a reduction in sensitivity to sulfur impurities. The test impression material of the present invention incorporating the complex B catalyst exhibited significantly reduced sulfur sensitivity, as indicated by its ability to fully set at surfaces in contact with a sulfur impurity. The test impression material of the present invention utilizing the complex A catalyst at least partially set at the contact surface after 10 minutes, although it did not fully set within 20 minutes after placement. In contrast, the control impression material utilizing the platinum complex catalyst did not set at all at the contact surface within 20 minutes of contacting the sulfur impurity. As defined in ISO specification 4823, a material has set when it develops a recovery from deformation of between 96.5% and 100%. Thus, while the bulk of the impression material may fully set within 10 minutes in each of the test and control materials, surfaces in contact with sulfur impurities may be prevented from setting due to the sulfur deactivating the catalyst, possibly by a chelation mechanism. The parent benzylidene ruthenium complex A caused a reduction in sulfur sensitivity, and the high ring-opening metathesis active ruthenium carbene complexes having substituted imidazole ligands exhibited the highest reduction in sulfur sensitivity during polymerization, as indicated by the full setting of the material at the contacting surface. Thus, compositions of the present invention including a ruthenium carbene complex with a ligand having a basicity higher than that of tricyclonexylphosphine can achieve a recovery after deformation of at least 96.5% within 20 minutes of contacting a thin film of an oxidizable sulfur-containing compound.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative methods and illustrative examples shown and described. Accordingly, departures may be made from such details without departing from the scope or spirit of applicant's general inventive concept.

What is claimed is:

1. A composition for use as a dental impression material, comprising:

a polymerizable resin comprising a telechelic oligomer or polymer curable by ring-opening metathesis polymerization;

a filler system selected from the group consisting of dental reinforcing filler, dental non-reinforcing filler, and combinations thereof; and a ruthenium carbene complex catalyst, wherein the catalyst is capable of initiating the ring-opening metathesis polymerization of the composition to form a cured dental impression material.

2. The composition of claim 1, wherein the polymerizable resin is telechelic polydimethylsiloxane end-functionalized with norbornenyl groups and having between about 5 and about 5000 dimethylsiloxane units.

3. The composition of claim 2, wherein the polydimethylsiloxane includes between about 27 and about 1590 dimethylsiloxane units.

4. The composition of claim 1, wherein the polymerizable resin is a telechelic polysiloxane having the following structure:

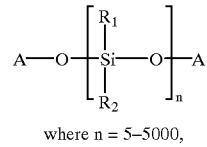

where n = 5–5000,

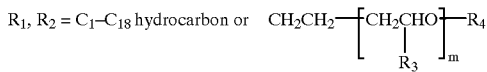

where $R_3$, $R_4$ = $C_1$–$C_{18}$ hydrocarbon, and m = 0–2; and

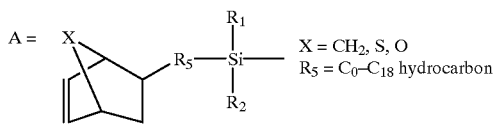

-continued

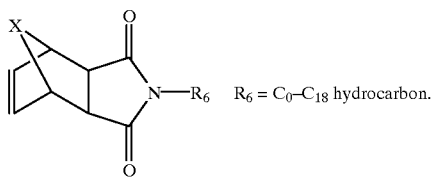 $R_6 = C_0–C_{18}$ hydrocarbon.

5. The composition of claim 1, wherein the polymerizable resin is telechelic polytetrahydrofuran-polyethylene oxide end-functionalized with norbornenyl groups.

6. The composition of claim 1, wherein the composition comprises about 5 wt. % to about 95 wt. % of the polymerizable resin.

7. The composition of claim 1, wherein the filler system is bimodal, having a sub-micron sized filler component and a micron sized filler component.

8. The composition of claim 7, wherein the composition comprises up to about 10 wt. % sub-micron sized filler and about 10 wt. % to about 60 wt. % micron sized filler.

9. The composition of claim 1, wherein the catalyst is a benzylidene ruthenium complex of the formula:

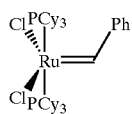 A wherein Cy is cyclohexyl and Ph is phenyl.

10. The composition of claim 1, wherein the catalyst is a 4,5-dihydroimidazol-2-ylidene-substituted ruthenium carbene complex.

11. The composition of claim 1, wherein the catalyst is a ruthenium carbene complex with one ligand having a basicity higher than tricyclohexylphosphine.

12. The composition of claim 11, wherein the complex is of the formula:

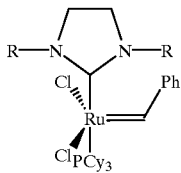 B wherein Cy is cyclohexyl, Ph is phenyl and R is mesityl.

13. The composition of claim 11, wherein the complex is of the formula:

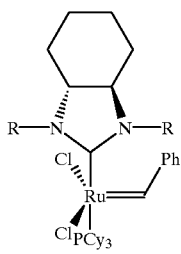 C wherein Cy is cyclohexyl, Ph is phenyl and R is mesityl.

14. The composition of claim 11, wherein the complex is of the formula:

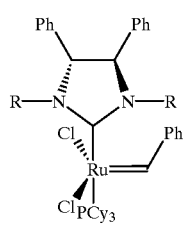 D wherein Cy is cyclohexyl, Ph is phenyl and R is mesityl.

15. The composition of claim 1, wherein the composition achieves a recovery after deformation of at least 96.5% within 20 minutes of contacting a film of an oxidizable sulfur-containing compound.

16. The composition of claim 1 wherein the composition comprises about 0.001 wt. % to about 1 wt. % of the catalyst.

17. A composition for use as a dental impression material, comprising;
 a base paste including a polymerizable resin that is a telechelic oligomer or polymer curable by ring-opening metathesis polymerization and a filler system; and
 a catalyst paste including a ruthenium carbene complex catalyst dissolved in a solvent which is miscible with the base paste, and a filler system, wherein the catalyst is capable of initiating the ring-opening metathesis polymerization of the composition to form a cured dental impression material,
  wherein the filler system in each of the base paste and catalyst paste are selected from the group consisting of dental reinforcing filler, dental non-reinforcing filler, and combinations thereof.

18. The composition of claim 17, wherein the ratio of the base paste to the catalyst paste in the composition is in the range of about 10:1 to about 1:10.

19. The composition of claim 17, wherein the polymerizable resin is telechelic polydimethylsiloxane end-functionalized with norbornenyl groups and having between about 5 and about 5000 dimethylsiloxane units.

20. The composition of claim 19, wherein the polydimethylsiloxane includes between about 27 and about 1590 dimethylsiloxane units.

21. The composition of claim 17, wherein the polymerizable resin is a telechelic polysiloxane having the following structure:

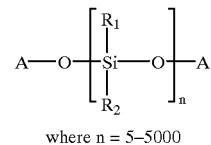

where n = 5–5000

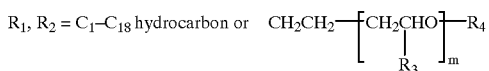

where $R_3, R_4 = C_1–C_{18}$ hydrocarbon, and m = 0–2; and

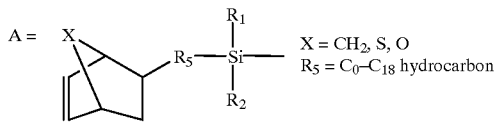

$X = CH_2, S, O$
$R_5 = C_0–C_{18}$ hydrocarbon

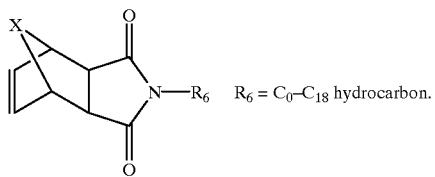

R_6 = C_0–C_18 hydrocarbon.

22. The composition of claim 17, wherein the polymerizable resin is telechelic polytetrahydrofuran-polyethylene oxide end-functionalized with norbornenyl groups.

23. The composition of claim 17, wherein the composition comprises about 5 wt. % to about 95 wt. % of the polymerizable resin.

24. The composition of claim 17, wherein the filler system in each of the base paste and the catalyst paste is bimodal, having a sub-micron sized filler component and a micron sized filler component.

25. The composition of claim 24, wherein the composition comprises up to about 10 wt. % sub-micron sized filler and about 10 wt. % to about 60 wt. % micron sized filler.

26. The composition of claim 17, wherein the catalyst is a benzylidene ruthenium complex of the formula:

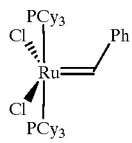

A wherein Cy is cyclohexyl and Ph is phenyl.

27. The composition of claim 17, wherein the catalyst is a 4,5-dihydroimidazol-2-ylidene-substituted ruthenium carbene complex.

28. The composition of claim 17, wherein the catalyst is a ruthenium carbene complex with one ligand having a basicity higher than tricyclohexylphosphine.

29. The composition of claim 28, wherein the complex is of the formula:

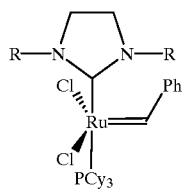

B wherein Cy is cyclohexyl, Ph is phenyl and R is mesityl.

30. The composition of claim 28, wherein the complex is of the formula:

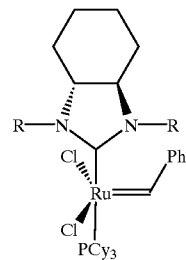

C wherein Cy is cyclohexyl, Ph is phenyl and R is mesityl.

31. The composition of claim 28, wherein the complex is of the formula:

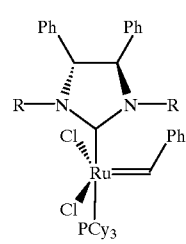

D wherein Cy is cyclohexyl, Ph is phenyl and R is mesityl.

32. The composition of claim 17, wherein the composition achieves a recovery after deformation of at least 96.5% within 20 minutes of contacting a film of an oxidizable sulfur-containing compound.

33. The composition of claim 17 wherein the composition comprises about 0.001 wt. % to about 1 wt. % of the catalyst.

34. A composition for use as a dental impression material, comprising:
a base paste including a telechelic polysiloxane curable by ring-opening metathesis polymerization and a filler system selected from the group consisting of dental reinforcing filler, dental non-reinforcing filler, and combinations thereof; and
a catalyst paste including a substituted ruthenium carbene complex with a substituted ligand having a basicity higher than tricyclohexylphosphine, the complex dissolved in a solvent which is miscible with the base paste, and a filler system selected from the group consisting of dental reinforcing filler, dental non-reinforcing, filler, and combinations thereof,
wherein the catalyst is capable of initiating the ring-opening metathesis polymerization of the composition to form a cured dental impression material, and
wherein the composition achieves a recovery after deformation of at least 96.5% within 20 minutes of contacting a solution of 1% or less of an oxidizable sulfur-containing compound in hexane.

* * * * *

UNITED STATES PATENT AND TRADEMARK OFFICE
CERTIFICATE OF CORRECTION

PATENT NO. : 6,455,029 B1
DATED : September 24, 2002
INVENTOR(S) : Angeletakis et al.

It is certified that error appears in the above-identified patent and that said Letters Patent is hereby corrected as shown below:

Column 1,
Line 55, reads "impunities" and should read -- impurities --.

Column 4,
Line 23, reads "micronsized" and should read -- micron-sized --.
Line 56, reads "norbornyl" and should read -- norbornenyl --.

Column 5,
Line 30, reads "27 average)" and should read -- 27 (average) --.

Column 6,
Line 40, reads "arc" and should read -- are --.
Line 49, reads "(2-ethylhexylthiolycolate)" and should read
-- (2-ethylhexylthioglycolate) --.

Column 12,
Line 49, reads "non-reinforcing, filler," and should read -- non-reinforcing filler, --.

Signed and Sealed this

Twenty-fifth Day of February, 2003

JAMES E. ROGAN
*Director of the United States Patent and Trademark Office*